US00PP34378P2

(12) United States Plant Patent
Koot

(10) Patent No.: US PP34,378 P2
(45) Date of Patent: Jun. 28, 2022

(54) ***BUDDLEJA* PLANT NAMED 'BOTEX 004'**

(50) Latin Name: *Buddleja davidii*
Varietal Denomination: 'Botex 004'

(71) Applicant: Botanic Experience B.V., Kaatsheuvel (NL)

(72) Inventor: Johannes Adrianus Maria Koot, Kaatsheuvel (NL)

(73) Assignee: BOTANIC EXPERIENCE B.V., Kaatsheuvel (NL)

( * ) Notice: Subject to any disclaimer, the term of this patent is extended or adjusted under 35 U.S.C. 154(b) by 0 days.

(21) Appl. No.: 17/557,039

(22) Filed: Dec. 20, 2021

(30) Foreign Application Priority Data

Dec. 23, 2020 (QZ) ..... PBR 20203392

(51) Int. Cl.
*A01H 5/02* (2018.01)
*A01H 6/00* (2018.01)

(52) U.S. Cl.
USPC ..... Plt./242

(58) Field of Classification Search
USPC ..... Plt./242
CPC ... A01H 5/02; A01H 5/00; A01H 6/00; A01H 6/14; A01H 6/30; A01H 6/50
See application file for complete search history.

*Primary Examiner* — June Hwu
(74) *Attorney, Agent, or Firm* — Penny J. Aguirre

(57) ABSTRACT

A new cultivar of *Buddleja* plant named 'Botex 004' that is characterized by its dense, compact, upright plant habit, its flowers that are lilac blue in color, its neat and naturally vase-like plant shape, its very floriferous blooming habit, and its flowers that have a pleasant fragrance.

2 Drawing Sheets

Botanical classification: *Buddleja davidii.*
Variety denomination: 'Botex 004'.

CROSS-REFERENCE TO A RELATED APPLICATION

This application claims priority to European Community Plant Variety Office (CPVO) Plant Breeder's Rights Application No. 2020/3392 filed on Dec. 23. 2020, under 35 U.S.C. 119(f), the entire contents of which is incorporated by reference herein. This application is also co-pending with a U.S. Plant Patent Application filed for a plant derived from the same breeding program from similar parentage that is entitled *Buddleja* Plant Named 'Botex 003' (U.S. Plant patent Ser. No. 17/557,032).

BACKGROUND OF THE INVENTION

The present invention relates to a new and distinct cultivar of *Buddleja davidii* will be referred to hereafter by its cultivar name, 'Botex 004'. 'Botex 004' is a new shrub grown for use as an ornamental landscape plant.

The new cultivar of *Buddleja* is a selection from an ongoing breeding program conducted by the Inventor in Kaatsheuvel, The Netherlands with the objective of creating new cultivars of *Buddleja* with very neat and compact plant habits combined with unique flower colors and floriferous blooming habits.

The Inventor made a cross in summer of 2018 between an unnamed proprietary plant in the Inventor's breeding program; reference no. 19019 as the female parent and reference no. 11013 as the male parent. The Inventor selected 'Botex 004', in summer of 2019 as a single unique plant amongst the seedlings that resulted from the above cross.

Asexual propagation of the new cultivar was first accomplished by the Inventor using stem cuttings in Kaatsheuvel, The Netherlands in August of 2019. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Botex 004' as a unique cultivar of *Buddleja.*

1. 'Botex 004' exhibits a dense, compact, upright plant habit.
2. 'Botex 004' exhibits flowers that are lilac blue in color.
3. 'Botex 004' exhibits a neat and naturally vase-like plant shape.
4. 'Botex 004' exhibits a very floriferous blooming habit.
5. 'Botex 004' exhibits flowers that have a pleasant fragrance.

The female parent of 'Botex 004' differs from 'Botex 004' in having inflorescences that are longer in length, flowers that are light purple in color, and in having a taller plant height. The male parent of 'Botex 004' differs from 'Botex 004' in having inflorescences that are shorter in length, a shorter plant height, and a less upright and more spreading plant habit. 'Botex 004' can be compared to the *Buddleja* cultivars 'Nanho Blue' (not patented) and 'Botex 003'. 'Nanho Blue' differs from 'Botex 004' in having a taller plant height and spreading to spreading-upright plant habit with longer arching branches, 'Botex 003' differs from 'Botex 004' in having flowers that are white in color.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosures include but may not be limited to website listings by Podoslonami, Groen Vandaag, Plantago, Greenport, Gabot, Bloemenkrant, Floricade, Plantipp, Hortipoint, CG Concept, Stad+Groen, Floranews, Tuinzaken, Handel & Techniek, Van Son & Koot BV, KVBC, Perishablenews, Hortweek, Buddlejagarden, Boom-in-Business, Greenity, and Obst & Garden.

BRIEF DESCRIPTION OF THE DRAWINGS

The accompanying color photographs illustrate the overall appearance and distinct characteristics of the new *Buddleja*. The photographs were taken of a one-year-old plant as grown in a greenhouse in a 19-cm container in Kaatsheuvel, The Netherlands.

The photograph in FIG. 1 provides a side view of the overall plant habit of 'Botex 004' in bloom.

Figure 1:
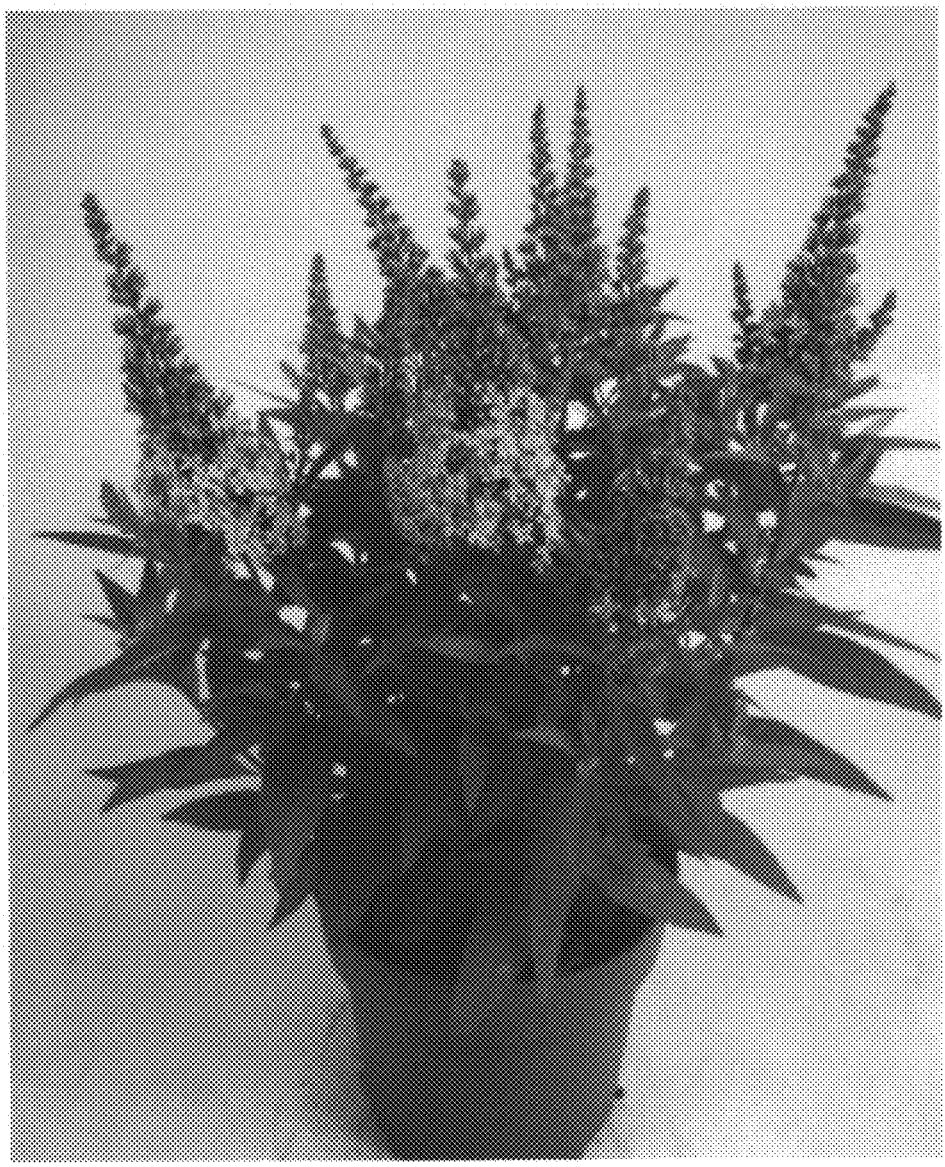
Figure 2:
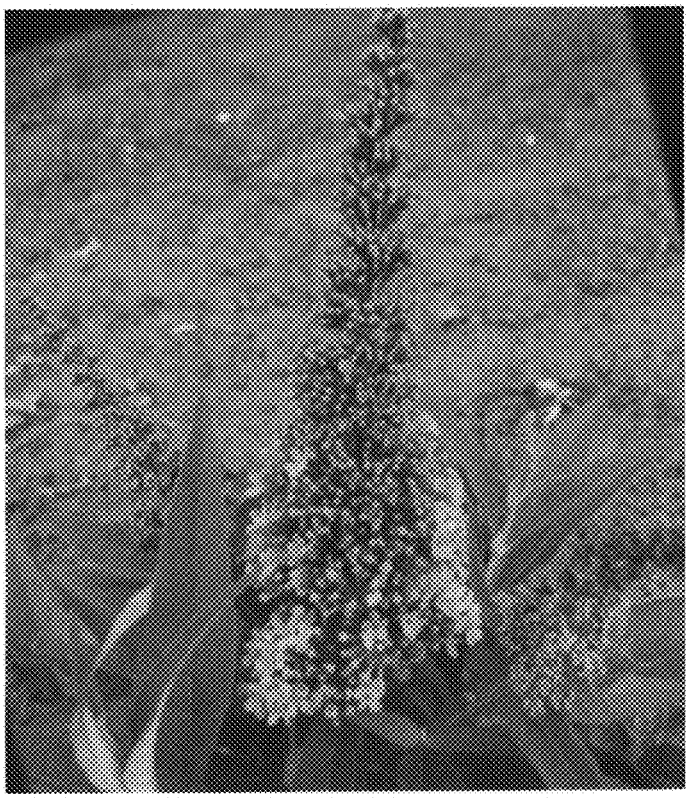

The photograph in FIG. 2 provides a close-up view of an inflorescence of 'Botex 004'.

Figure 3:
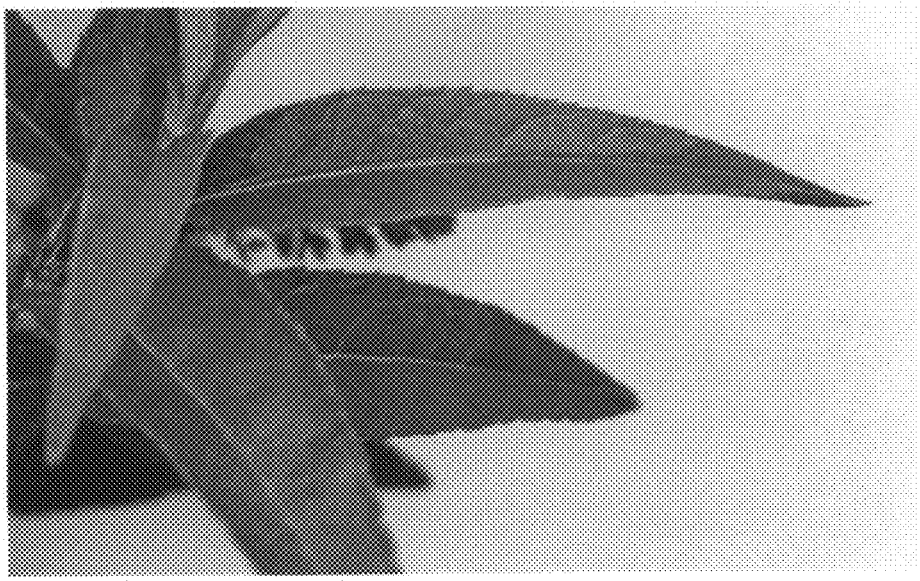

The photograph in FIG. 3 provides a close-up view of the foliage of 'Botex 004'.

The colors in the photographs are as close as possible with the photographic and printing technology utilized and the color values cited in the Detailed Botanical Description accurately describe the colors of the new *Buddleja*.

DETAILED BOTANICAL DESCRIPTION

The following is a detailed description of one-year-old plants as grown in a greenhouse in 19-cm containers in Kaatsheuvel, The Netherlands. The phenotype of the new cultivar may vary with variations in environmental, climatic, and cultural conditions, as it has not been tested under all possible environmental conditions. The color determination is in accordance with the 2015 Colour Chart of The Royal Horticultural Society, London, England, except where general color terms of ordinary dictionary significance are used.

General description:

*Blooming period*.—July to October in The Netherlands.

*Plant type*.—Deciduous perennial shrub.

*Plant habit*.—Compact, upright, dense.

*Plant size*.—An average of 31 cm in height and 48 cm in width and reaches 80 cm in height and 80 to 90 cm in spread as grown in the landscape.

*Cold hardiness*.—At least in U.S.D.A. Zone 5.

*Diseases and pests*.—No susceptibility and resistance to diseases or pests has been observed.

*Propagation*.—Stem cuttings.

*Root description*.—Fibrous.

*Root development*.—An average of 8 weeks to initiate roots and eight weeks to fully root as a young plant in a P9 container.

*Growth rate*.—Vigorous.

Branch description:

*Branch shape*.—Quadrangular.

*Branch color*.—Young stems; 145B, mature stems; 199A.

*Branch strength*.—Strong.

*Branch size*.—An average of 20 cm in length and 4 mm in diameter.

*Branch surface*.—Pubescent.

*Branch aspect*.—Lateral stems held upright to 20° from vertical.

*Branch internode length*.—Average of 2 cm.

*Branching*.—Basal branching; 3 main branches, 12 secondary branches.

Foliage description:

*Leaf shape*.—Narrowly elliptical to elliptical.

*Leaf division*.—Simple.

*Leaf base*.—Attenuate.

*Leaf apex*.—Acute.

*Leaf fragrance*.—None.

*Leaf venation*.—Pinnate, color; upper surface 144A, lower surface 191D, main vein 145B.

*Leaf margins*.—Serrate.

*Leaf arrangement*.—Opposite.

*Leaf attachment*.—Petiolate.

*Leaf surface*.—Both sides are matte, and pubescent.

*Leaf size*.—An average of 9.7 cm in length and 2.7 cm in width.

*Leaf quantity*.—An average of 12 per stem.

*Leaf color*.—Young upper surface; 137C, base 145C, young lower surface; 191A, mature upper surface; 137A, mature lower surface; 191D.

*Petioles*.—An average of 6 mm in length and 2 mm in diameter, medium to high strength, both surfaces 145B in color, both surfaces and slightly pubescent.

Inflorescence description:

*Inflorescence type*.—Compound terminal and axial panicles.

*Inflorescence size*.—An average of 11.5 cm in height, 6.5 cm in width.

*Flower fragrance*.—Sweet, pleasant and medium strength.

*Lastingness of flowers*.—An average of 5 days, persistent, inflorescence is semi-indeterminate.

*Flower buds*.—Oblong, average of 4 mm in length and 1 mm in diameter, color; 157B, mature buds are flushed with 85A.

*Flower aspect*.—Upright.

*Flower quantity*.—An average of 150 flowers per inflorescence.

*Flower type*.—Single, salverform.

*Flower surface*.—All surfaces glabrous and smooth.

*Flower size*.—An average of 7 mm in height, 1.2 cm in diameter, flower throat; 4 mm in length, 1 mm in diameter, flower tube; 3 mm in length, 1 mm in diameter.

*Peduncles*.—An average of 2.2 cm in length and 2.5 mm in diameter, held erect, 145A in color, strong, glossy and pubescent surface.

*Pedicels*.—An average of 2 mm in length and 1 mm in diameter, held at an average angle of 45°, 145B in color, strong, surface is glossy and pubescent.

*Calyx*.—Campanulate in shape, an average of 2 mm in depth and 1 mm in diameter.

*Sepals*.—4, 1 whorl, rotate arrangement, fused into a campanulate shape, 3.5 mm in length, 1.5 mm in width, lanceolate in shape, acute apex, fused base, entire margin, both surfaces are matte and slightly pubescent, color; when opening and fully open upper and lower surface 145A.

*Petals*.—Average of 4, rotate, fused into salverform, 1 whorl, roughly spathulate in shape, slightly undulate margin, rounded apex, an average of 3 mm in length and width, outer and inner surface is glabrous and matte, color; upper and lower surface when opening and fully open 85A, base 23A, flower throat 85A, flower tube 15D, base 85A, towards the throat a hint of 83B.

Reproductive organs:

*Gynoecium*.—1 pistil, 3 mm in length, style; an average of 2 mm in length, 145D in color, stigma; elongated, 1 mm in length and 145B in color, ovary is 145D in color.

*Androcoecium*.—Stamens; 4, filament; 4 mm in length and 20B in color, anther; ovate in shape, 1 mm in length, 11D in color, pollen; low in quantity, 11D in color.

*Fruit and seed*.—No seeds or fruit have been observed to date.

It is claimed:

1. A new and distinct cultivar of *Buddleja* plant named 'Botex 004' as herein illustrated and described.

* * * * *